US00PP13616P29

(12) United States Plant Patent
Vardi et al.

(10) Patent No.: US PP13,616 P2
(45) Date of Patent: Mar. 4, 2003

(54) CITRUS TREE NAMED 'ORRI'

(75) Inventors: Aliza Vardi, Ramat Gan (IL); Pinchas Spiegel-Roy, Ramat-Gan (IL); Ahuva Frydman-Shani, Ramat-Gan (IL); Avraham Elchanati, Holon (IL); Hana Neumann, Hemed (IL)

(73) Assignee: State of Israel-Ministry of Agriculture and Rural Development, Tel Aviv (IL)

( * ) Notice: Subject to any disclaimer, the term of this patent is extended or adjusted under 35 U.S.C. 154(b) by 0 days.

(21) Appl. No.: 09/716,482

(22) Filed: Nov. 20, 2000

(51) Int. Cl.[7] ..... A01H 5/00
(52) U.S. Cl. ..... Plt./202
(58) Field of Search ..... Plt./202

(56) References Cited

PUBLICATIONS

GTITM OPOVROM Citation for 'ORRI' as per IL PBR 02641; Feb. 26, 1999.*

* cited by examiner

*Primary Examiner*—Kent L. Bell
(74) *Attorney, Agent, or Firm*—Akerman Senterfitt

(57) ABSTRACT

A new variety of mandarin citrus tree is described that is distinguished by fruit having zero or few seeds, flowers having anthers bearing pollen with low pollen fertility, and a long ripening period from the beginning of January to the end of April.

2 Drawing Sheets

FIELD OF THE INVENTION

A new mandarin cultivar *Citrus reticulata* hybrid is described. The new variety named 'Orri' is desirable to the consumer because it typically has zero or few seeds (0–6 seeds per fruit) and to the grower because of a long ripening period. The fruit has typical flavor with low to moderate acidity.

BACKGROUND OF THE NEW PLANT

The present invention relates to a new variety of mandarin tree *Citrus reticulata* hybrid developed by inventors Aliza Vardi, Pinchas Spiegel-Roy, Avraham Elchanati, Ahuva Frydman-Shani, and Hana Neumann in 1988–1994 in Bet Dagan, Israel from a selection of plants grown from irradiated bud wood of the cultivar 'Orah' (unpatented).

Asexual reproduction of the new variety in Israel by grafting has shown that the new characteristics are stabilized and permanently fixed through successive propagation.

The objective in breeding the present new tree variety, assigned the denomination 'Orri' was to obtain a late ripening mandarin citrus fruit with few or no seeds. In the spring of 1987 and 1988 about 300 buds of an easy peeling mandarin cultivar, 'Orah' were irradiated at the Nahal Soreq Nuclear Center, Yavne, Israel, by exposure to 3.5 kh of gamma radiation from a Co60 source. Sour orange nucellar rootstocks were bud grafted with the individual buds of irradiated 'Orah' bud wood and labeled $mV_1$. Six to nine months after grafting the irradiated budwood, individual buds from the $mV_1$ plants were re-grafted on Sour orange nucellar rootstocks to establish about 550 $mV_2$ plants.

Field planting was established from container grown $mV_2$ plants in the spring of 1989 and in the spring of 1990. The first fruits were observed in January–March, 1992 and a second observation of the fruits was again made in 1993 and 1994.

One of the selections, 1/24/27, had medium size orange color fruit and was easy to peel. This selection was distinguished from 'Orah' in having 0–4 seeds per fruit compared to 9–25 seeds per fruit for 'Orah' and having low pollen fertility. Typically, 12.5% of pollen grains of 1/24/27 were stained with acetocarmine compared with 89% for 'Orah'.

SUMMARY OF THE INVENTION

Table 1 shows some of the characteristics of the new mandarin citrus, designated 'Orri' compared with the parent 'Orah'.

TABLE 1

| Tree | Fruit color | Peelability | Seeds/fruit | Pollen fertility[1] |
|---|---|---|---|---|
| 1/24/27 'Orri' | Orange RHS 23B | easy | 0–4 | 12.5% |
| 'Orah' | Orange RHS 23B | easy | 9–25 | 89.0% |

[1]Estimated by Acetocarmine staining

The following is a detailed description of the new mandarin citrus variety based on observations made under typical Israeli grove conditions.

'Orri' is similar in tree shape and fruit appearance to 'Orah'. The tree is vigorous. Small thorns, 1–3 mm, are usually present in the leafy part of the branches, especially in the lower portion and on the lower part of fruit bearing branches. Main branches have an upright attitude and young shoots have no anthocyanin coloration at the tip.

The bearing of the tree is regular and productivity is relatively high, about the same as for 'Orah'. The canopy is moderately dense. The bark of the young shoots is initially smooth and green gradually turning into a smooth greyed-green color.

The leaves are similar to 'Orah'. They are lanceolate and small to medium in size. The leaf blade is firm without undulation and slightly concave in cross section. Petioles are without wings.

The characteristics of the flowering and the flower parts are also similar to those of 'Orah'. Flowering for both occurs at the end of March or April in Bet Dagan, Israel. Both 'Orri' and 'Orah' produce about the same number of flowers. Flower drop for both occurs in April. Flowers are borne singly and have an average number of stamens (about 20) with complete style development.

Anther color is pale yellow to white. Pollen fertility is low as indicated by the observation that only 12.5% of the pollen grains were stained with acetocarmine in a test conducted at the Agricultural Research Organization, the Volcani Center, as compared with stainability of about 89% for 'Orah' pollen grain.

The fruit has zero or few seeds (0–4 seeds per fruit) even when optimal pollination conditions are employed. This compares with about 9–27 seeds per fruit in 'Orah'. The fruit shape is oblate and medium size. When 50 fruits were measured, the fruit had an average weight of 140 g, an average height of 58 mm and an average diameter of 66 mm. The fruit has a moderately depressed stalk end. The fruit surface is usually smooth with a yellow orange color, RHS 23B on The Royal Horticultural Society of London Colour Chart, and bears an average number of conspicuous rind oil glands. Fruit ripening does not differ from outside of the canopy to the inside, but the fruit color of the outside canopy is a little brighter as compared to the fruit color of the inside canopy. There is no persistence of the style and the areola is not completely developed. A navel is absent. The rind is thin and easy to peel.

The color of the albedo is yellow-orange and the flesh is orange in color. The fruit contains 9–11 segments and is very juicy. The external color of the seeds (when fresh) and dry is yellowish. The internal seed coat is white-yellow and the cotyledons are white. Monoembryonic seeds are present (one embryo per seed).

The seed size, shape and texture are also similar to the parent 'Orah'. The fruit reaches maturity late in the season as does 'Orah', which in Israel is mid-January to April. The ripening of the fruit within the canopy is uniform. Fruit remaining on the tree does not regreen and does not begin to lose quality until end of April. If there is a heavy crop and the fruits are not picked before April, the tree may becomes an alternate bearing and have a low fruit yield after a year of heavy crop. Pre-harvest drop of developed and undeveloped fruit is similar to that of the parent cultivar 'Orah'.

DESCRIPTION OF THE PHOTOGRAPHS

The new citrus tree is illustrated in the accompanying color photographs.

Sheet one depicts the whole tree and canopy shape of the new variety.

Sheet two shows the new variety with the whole fruit, illustrating the exterior of the fruit as well as transverse midsections in a plane substantially perpendicular to the axis, illustrating no seeds in the interior of the fruit.

DESCRIPTION OF THE NEW TREE

The following is a detailed description of the new mandarin citrus variety 'Orri' based on observations made under typical Israeli grove conditions. Observations were made on trees approximately 4–5 years old. All color descriptions are by RHS color designation as set forth in The R.H.S. Colour Chart published by The Royal Horticultural Society, London.

Tree:

*Origin.*—Irradiation of cv. 'Orah'.

*Classification.*—Botanical: *Citrus reticulata* hybrid. Common: Mandarin citrus. Curlivar: 'Orri'.

*Shape.*—Vigorous, upright, somewhat spreading.

*Thorns.*—1–3 mm length (present on leafy part of branches).

*Branching.*—Upright.

*Canopy.*—Moderately dense.

*Bark.*—Immature: smooth and green, RHS 137B. Mature: smooth and grayed-green, RHS 197 A to RHS 197 B.

*Leaf.*—Lanceolate. Size: small to medium (83 mm length, 36 mm width). Leaf blade: firm, concave in cross section, sharp end. Petioles: Wingless 16 mm length, 3 mm in diameter, Green RHS 146B. Color: Green RHS 146A (upper), Green RHS 146B (lower).

*Habit.*—Vigorous.

*Height.*—3 m.

*Disease resistance.*—No particular susceptibility or resistance observed.

*Tree spread.*—Pruning of orchard makes tree spread diameter difficult to measure.

*Trunk diameter.*—11 cm at 20 cm above the ground.

*Winter hardiness.*—Winter temperature in Bet Dagan, Israel averages 4–7 degrees Centigrade.

Flower:

*Petals.*—5.

*Petal color.*—White RHS 155D.

*Pistils.*—1.

*Flowering period.*—Late March or early April under growing conditions in Bet Dagan, Israel.

*Flower drop.*—Late April or early May under growing conditions in Bet Dagan, Israel.

*Stamens.*—20 (complete style).

*Anther color.*—Pale yellow, RHS 8C.

*Pollen fertility.*—Low (12.5% as indicated by acetocarmine staining).

*Anthocyanin coloration.*—No coloration on terminal buds.

Fruit:

*Shape.*—Oblate Apex: flat; Base: rounded, no neck.

*Size.*—Medium.

*Weight.*—140 g.

*Height.*—58 mm.

*Diameter.*—66 mm.

*Skin color.*—Yellow-orange, RHS 23B.

*Rind oil gland.*—Moderately conspicuous (aveage number/$cm^2$ 20).

*Style.*—No persistence, incomplete development of areola.

*Navel.*—Absent.

*Rind.*—Thin (2–3 mm) and easily peelable.

*Albedo.*—Yellow-orange, RHS 18C.

*Flesh color.*—Yellow-orange RHS 23A.

*Fruit segments.*—9–11.

*Time to maturity.*—3–4 months (January–April).

*Productivity.*—70 kg/tree per season (January–April in Israel).

*Fruit extract.*—(Tested March 1994 on juice of representative ripe fruit). Total soluble solids (TSS) 14%. Acid content: 0.7%. TSS/acid ratio 20. Flavor: pleasant sweetness.

Seeds:

*Color.*—External: Yellow-white RHS 159 C. Internal: Yellow-white RHS 159A.

*Cotyledons.*—White, RHS 158 B to White, RHS 158 C.

*Monoembryonic.*—1 embryo per seed.

The tree and its fruit as described herein may vary in slight detail due to climate and/or soil conditions under which the variety is grown. All observations were made at the Volcani Center, Bet Dagen, Israel.

What is claimed is:

1. A new and distinct variety of *Citrus reticulata* hybrid tree substantially as herein described and shown.

* * * * *

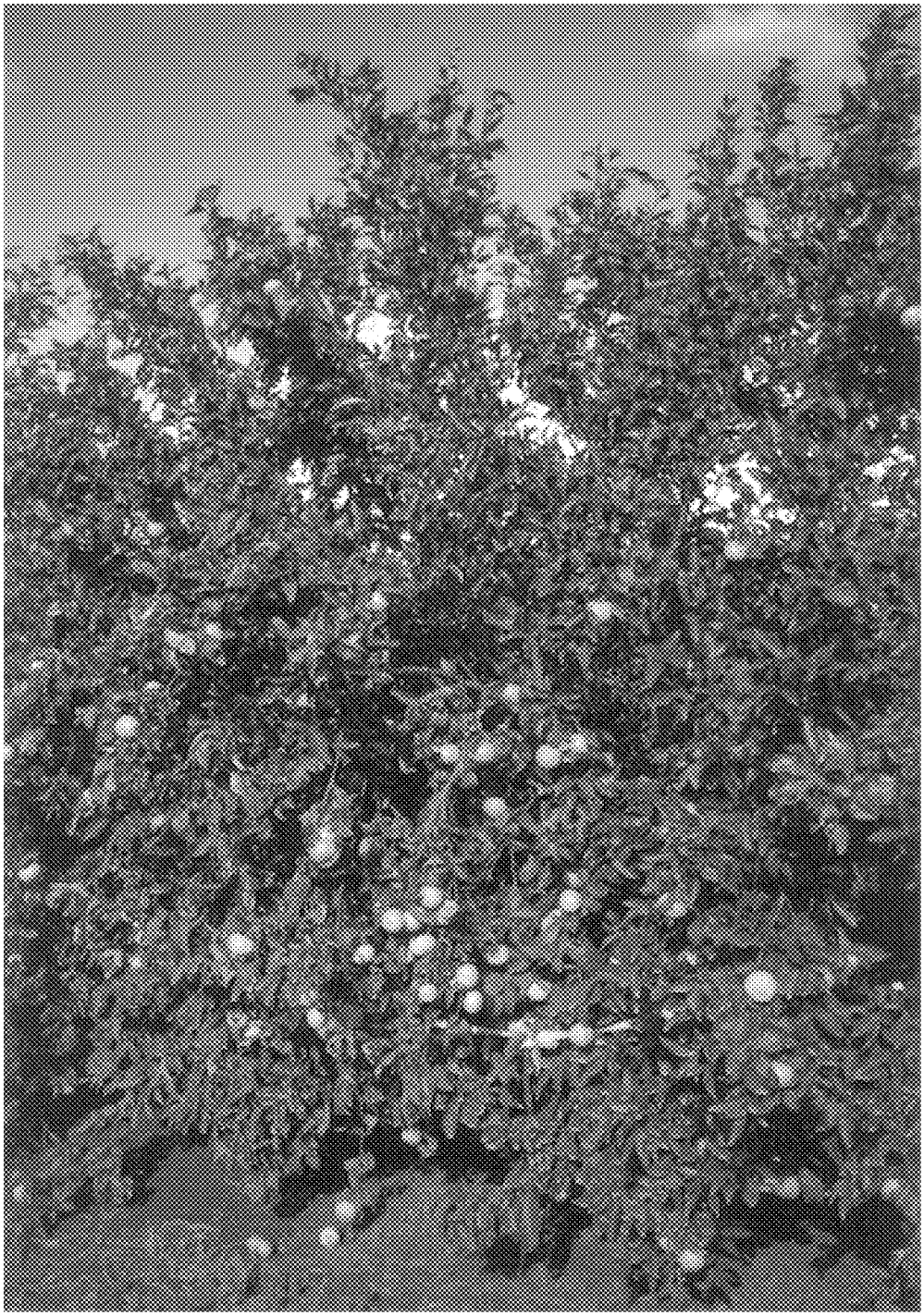

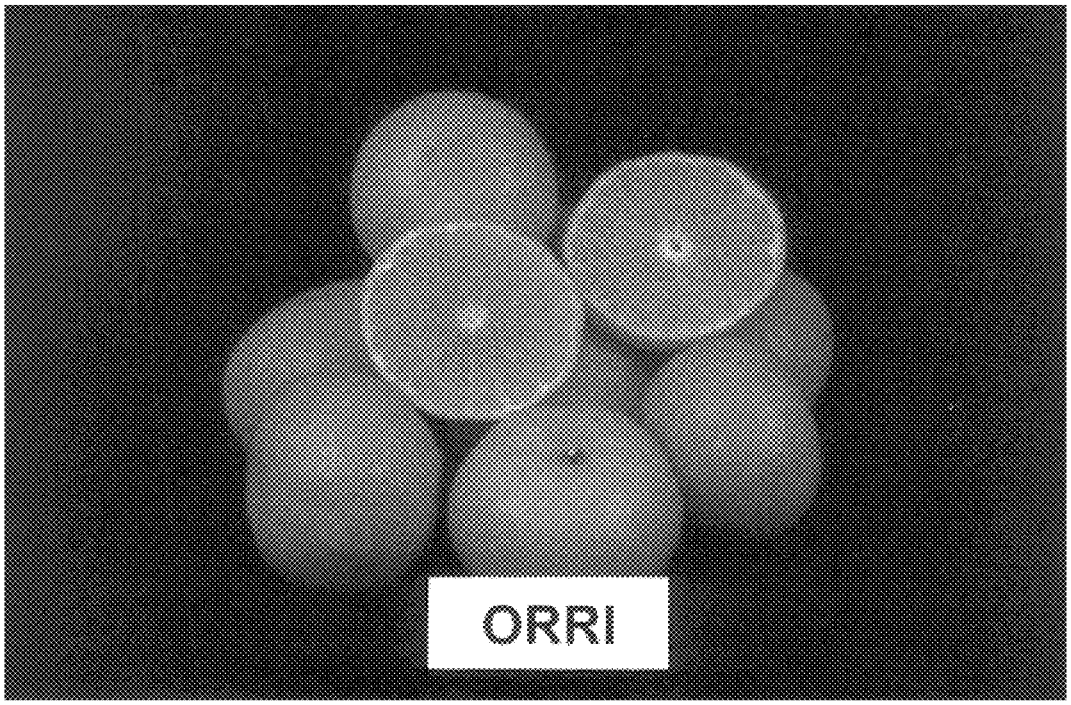
ORRI